(12) United States Patent
Weber et al.

(10) Patent No.: US 8,529,539 B2
(45) Date of Patent: Sep. 10, 2013

(54) MEDICAL DEVICES EMPLOYING ELECTROACTIVE POLYMERS FOR DELIVERY OF PARTICULATE THERAPEUTIC AGENTS

(75) Inventors: Jan Weber, Maastricht (NL); Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 259 days.

(21) Appl. No.: 13/101,301

(22) Filed: May 5, 2011

(65) Prior Publication Data

US 2011/0275980 A1   Nov. 10, 2011

Related U.S. Application Data

(60) Provisional application No. 61/332,544, filed on May 7, 2010.

(51) Int. Cl.
*A61M 31/00* (2006.01)
(52) U.S. Cl.
USPC .................. 604/501; 604/103.02; 424/426
(58) Field of Classification Search
USPC ....... 604/103.02, 501, 93.01, 891.1; 424/426
See application file for complete search history.

(56) References Cited

U.S. PATENT DOCUMENTS

| 5,733,925 | A | 3/1998 | Kunz et al. |
| 6,676,987 | B2 | 1/2004 | Zhong et al. |
| 7,048,962 | B2 | 5/2006 | Shekalim et al. |
| 2005/0165439 | A1 | 7/2005 | Weber et al. |
| 2006/0184092 | A1* | 8/2006 | Atanasoska et al. ............ 604/20 |
| 2006/0206188 | A1 | 9/2006 | Weber et al. |
| 2007/0112331 | A1 | 5/2007 | Weber et al. |
| 2007/0239256 | A1 | 10/2007 | Weber et al. |
| 2009/0318848 | A1 | 12/2009 | Shippy, III et al. |
| 2010/0087783 | A1 | 4/2010 | Weber et al. |

OTHER PUBLICATIONS

Han Xu, et al., "Polymer actuator valves toward controlled drug delivery application", Biosensors and Bioelectronics 21 (2006) 2094-2099.
E.W.H. Jager et al., "On-chip microelectrodes for electrochemistry with moveable PPy bilayer actuators as working electrodes", Sensors and Actuators B 56 (1999) pp. 73-78.
Moore et al., "Transcutaneous RF-Powered Implantable Minipump Driven by a Class-E Transmitter", IEEE Trans. Biomed Eng., Aug. 2006; 53 (8) pp. 1705-1708.
Smela, et al., "Volume Change in Polypyrrole Studied by Atomic Force Microscopy", J. Phys. Chem. B, 105 (2001) pp. 9395-9405.
Causley et al., "Electrochemically-induced fluid movement using polypyrrole", Synthetic Metals 151 (2005) pp. 60-64.
Naoi et al., "Quartz Crystal Microbalance Study: Ionic Motion Across Conducting Polymers", J. Electrochem. Soc., vol. 138, No. 2, Feb. 1991, pp. 440-445.

* cited by examiner

*Primary Examiner* — Kevin C Sirmons
*Assistant Examiner* — Deanna K Hall
(74) *Attorney, Agent, or Firm* — Mayer & Williams PC; David B. Bonham (57) ABSTRACT

In accordance with one aspect, medical devices are provided which comprise an electroactive polymer material and therapeutic-agent containing particles. The device is configured such that the particles are delivered from the device upon actuation of the electroactive polymer material.

20 Claims, 3 Drawing Sheets

MEDICAL DEVICES EMPLOYING ELECTROACTIVE POLYMERS FOR DELIVERY OF PARTICULATE THERAPEUTIC AGENTS

RELATED APPLICATIONS

This application claims priority from U.S. provisional application 61/332,544, filed May 7, 2010, which is incorporated by reference herein in its entirety.

FIELD OF THE INVENTION

The present invention relates to medical devices for the delivery of particulate therapeutic agents into human subjects.

BACKGROUND OF THE INVENTION

The delivery of a therapeutic agent onto or within the body of a patient is common in the practice of modern medicine. In vivo delivery of therapeutic agents is often implemented using medical devices that may be temporarily or permanently placed at a target site within the body. These medical devices can be maintained, as required, at their target sites for short or prolonged periods of time, delivering therapeutic agents at the target site.

SUMMARY OF THE INVENTION

In one aspect, the present disclosure is directed to medical devices which comprise an electroactive polymer material and therapeutic-agent containing particles. The device is configured such that the particles are delivered from the device upon actuation of the electroactive polymer material.

In one embodiment, the medical device comprises: a surface with at least one depression; an electroactive polymer material positioned in the depression and configured for electrical communication with a source of electrical power; and particles comprising a therapeutic agent disposed within the depression over the electroactive polymer material. When the electroactive polymer material is electrically actuated, the electroactive polymer material pushes the particles out of the device.

Advantages of medical devices in accordance with the present disclosure include one or more of the following: (a) the ability to achieve fast and efficient transfer of therapeutic agent into tissue, (b) the ability to deliver a predefined amount of therapeutic agent uniformly into tissue, (c) the ability to deliver drug into tissue whereby there is minimal loss prior to electroactive polymer actuation, and (d) the ability to provide for sustained presence of therapeutic agent in the tissue for days or weeks after delivery of the particles (depending on the release characteristics of the particles).

These and other aspects, embodiments and advantages will become readily apparent to those of ordinary skill in the art upon review of the Detailed Description and any claims to follow.

BRIEF DESCRIPTION OF THE DRAWINGS

FIG. 4C represents a cross-sectional view taken along line B-B of either FIG. 2 or FIG. 3.

DETAILED DESCRIPTION

A more complete understanding of the present invention is available by reference to the following detailed description of various aspects and embodiments of the invention. The detailed description of the invention which follows is intended to illustrate but not limit the invention. The scope of the invention is defined by any appended claims.

In accordance with one aspect, medical devices are provided which comprise an electroactive polymer material and therapeutic-agent containing particles. The device is configured such that the particles are delivered from the device upon actuation of the electroactive polymer material.

For instance, an implantable or insertable medical device may be provided, which comprises (a) a surface with at least one depression, (b) an electroactive polymer material positioned in the depression and adapted for electrical communication with a source of electrical power, and (c) particles comprising a therapeutic agent disposed within the depression over the electroactive polymer material. Upon electrical actuation of the electroactive polymer material, the particles are delivered from the device.

Figure 1A:
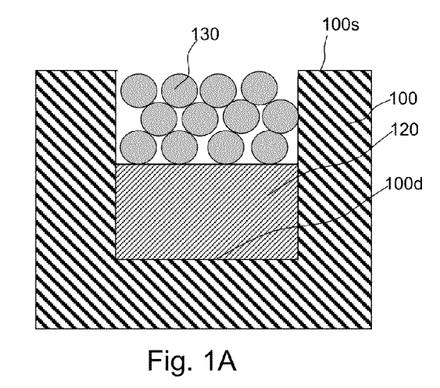
FIG. 1A is a schematic cross-sectional view of a portion of a medical device in accordance with an embodiment of the present disclosure.
Figure 1B:
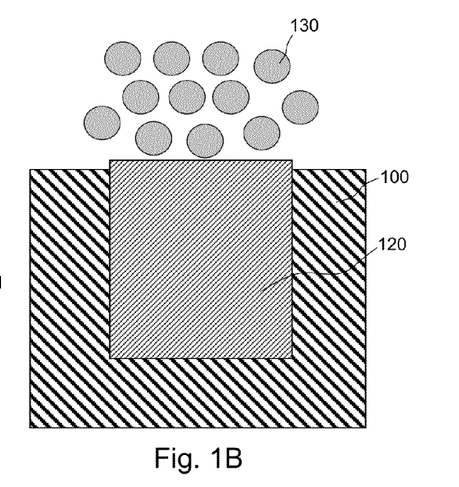
FIG. 1B illustrates the device of FIG. 1A after actuation of an electroactive polymer material within the device, such that therapeutic agent particles are driven from the device.

As a specific example, FIG. 1A is a schematic cross-section of a portion of a medical device 100 in accordance with an embodiment of the disclosure. The medical device 100 comprises a surface 100s with at least one depression 100d. An electroactive polymer material 120 is positioned in the bottom of the depression 100d, but does not completely fill the depression 100d. Disposed within the depression over the electroactive polymer material 120 are therapeutic-agent containing particles 130. Upon electrical actuation of the electroactive polymer material 120, the electroactive polymer material 120 expands in volume as shown in FIG. 1B, thereby pushing the particles 130 from the depression.

Medical devices benefiting from embodiments of the present disclosure are numerous and may be selected, for example, from the following: patches for delivery of therapeutic agent to intact skin and broken skin (including wounds), implantable or insertable medical devices such as balloons, catheters (e.g., expandable catheters such as balloon catheters), guide wires, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, embolization devices including cerebral aneurysm filler coils (such as Guglilmi detachable coils and various other metal coils), myocardial plugs, septal defect closure devices, implantable patches, drug depots that are adapted for placement in an artery for treatment of the portion of the artery distal to the device, pacemakers and pacemaker leads, defibrillation leads and coils, neurostimulation leads, ventricular assist devices including left ventricular assist hearts and pumps, total artificial hearts, heart valves, vascular valves, anastomosis clips and rings, cochlear implants, tissue bulking devices, tissue engineering scaffolds for in vivo tissue regeneration, especially neural pathway regeneration, such as the spinal cord, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, biopsy devices, as well as many other devices that are implanted or inserted into the body and from which therapeutic agent is released.

The medical devices of the present disclosure include medical devices that are used for diagnosis, for systemic treatment, or for the localized treatment of a tissue or organ, for example, selected from the following: tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, and cartilage. As used herein, "treatment" refers to the prevention of a disease or condition, the reduction or elimination of signs or symptoms associated with a disease or condition, or the substantial or complete elimination of a disease or condition. Typical subjects (also referred to as "patients") are vertebrate subjects, more typically mammalian subjects, and even more typically human subjects.

As noted above, in one aspect, embodiments of the present disclosure relate to medical devices which comprise an electroactive polymer material. The devices can be configured such that the therapeutic-agent containing particles are delivered from the device upon actuation of the electroactive polymer material. In some embodiments, the devices of the disclosure can be configured such that actuation results in an increase in volume (i.e., swelling) of the electroactive polymer material, which can lead to delivery of the particles.

An electroactive polymer material may actuated, for example, by application of a suitable potential between the electroactive polymer material and a counter-electrode that is positioned on or in the body. The following elements are generally utilized in this process: (a) the electroactive polymer material (which functions as a working electrode), (b) the counter-electrode, (c) an electrolyte in contact with both the electroactive polymer material and the counter-electrode, and (d) a source of electrical potential (also referred to herein as a "power supply").

The electrolyte, which is in contact with at least a portion of the surface of the electroactive polymer material, allows for the flow of ions and thus acts as a source/sink for the ions. The electrolyte may be, for example, a liquid, a gel, or a solid, so long as ion movement is permitted. In various embodiments, physiological fluid can be used as the electrolyte.

The counter-electrode may be disposed on or in the medical device, or it may be in the form of a distinct device. Counter-electrodes may be formed from a suitable conductive material. Examples of conductive materials for counter-electrodes include suitable members of the following, among many others: electroactive polymers such as those described herein, conductive carbon, metals and metal alloys, for example, gold, platinum, platinum alloys, and stainless steel, among others (due to their high conductivity, oxidation resistance, and radio-opacity, which may facilitate visibility of the device during fluoroscopy or the like) and copper, silver, zinc, iron, magnesium and alloys of the same (which can be left in the tissue where they will eventually oxidize in vivo). Counter-electrodes may take on innumerable shapes, including layers, rods, wires, tubes, blades, and grids, among many others. Designs maximizing the area of contact between the counter-electrode and the electrolyte may improve charge transfer and reduce activation time. In many embodiments, the counter-electrode is positioned as closely as possible to the electroactive polymer material.

In certain embodiments, the oxidation state of the electroactive polymer can be changed with the assistance of a reference electrode (e.g., a silver-based electrode, copper-based electrode, etc.). Like the counter-electrode, where employed, the reference electrode may be disposed on or in the medical device, or it may be in the form of a distinct device. In one embodiment, a silver/silver chloride (Ag/AgCl) reference electrode may be formed on the medical device using a process described in E. W. H. Jager et al., *Sensors and Actuators B* 56 (1999) 73-78. Specifically, an Ag/AgCl reference electrode may be formed by depositing (e.g., by electroplating or another deposition process) an Ag layer on the device (e.g., on a gold conductor layer), followed by partial conversion of the Ag layer to AgCl electrochemically, for example, by applying a suitable potential to the electrode while immersed in a potassium chloride (KCl) electrolyte solution (i.e., using a suitable counter-electrode).

A power supply may be, for example, provided within the medical devices of the present disclosure. Alternatively, a power supply may be, for example, provided within a separate device (e.g., a device that remains exterior to the subject, for instance, a console or other device that is operable by a healthcare provider) that is configured for connection to the medical devices of the present disclosure (e.g., via insulated conductive lines). In certain embodiments, the electroactive polymer material, the counter-electrode and the optional reference electrode are configured for ready electrical connection to a power supply, for instance, via insulated conductive lines that terminate in suitable electrical coupling components, for instance male or female electrical connection components, plugs, sockets, etc.

In certain devices of the present disclosure (e.g., expandable devices such as balloons, stents, etc.), medical devices may be provided with a piezoelectric material which actuates the electroactive polymer material when piezoelectric material is subjected to mechanical stress (e.g., compressive stress as a result of device expansion). More particularly, the application of the stress leads to the development of a voltage across the piezoelectric material, which voltage is used to actuate the electroactive polymer material.

In certain devices of the present disclosure, particularly implants, power may be provided in the form of a wireless system. For example, a device may be provided with a circuit that includes a conductive coil with a diode bridge in which one end is electrically connected to one or more electroactive polymer materials and another end is connected to one or more counter-electrodes. Such a system can be activated using an external power transmitter such as an RF transmitter. See, e.g., William H. Moore et al., *IEEE Trans Biomed Eng.* 2006 August; 53(8): 1705-1708. Suitable frequencies range, for example, from 1 megahertz (MHz) to 20 MHz. In certain embodiments, one may include additional electronic components, such as a voltage regulating device. A very useful component that can be used for this purpose is a Zener diode. Zener diodes are widely used to regulate the voltage across a circuit. When connected in parallel with a variable voltage source (e.g., a coil/diode arrangement like that previously described) so that it is reverse biased, a Zener diode begins to conduct current when the voltage reaches the diode's reverse breakdown voltage. From that point it maintains the voltage at that value. In other words, when receiving a variable voltage from a conductive coil, one can assure a fixed voltage across the electrodes regulating therapeutic agent release. Additional electronic components that may be employed include sensing devices (e.g., current and/or voltage sensing devices) and transmitters. With such components, one can communicate values (e.g., current and/or voltage values) back to the external power transmitter, allowing one to adjust the same. Such embodiments may be especially suitable for the larger implants (e.g., heart valves, tissue bulking and regeneration devices, etc.).

The electroactive polymer materials of the devices of the present disclosure may be formed using any suitable electroactive polymer. Electroactive polymers for use in the present disclosure include conductive polymers. Known conductive polymers include polypyrrole and its derivatives and copolymers, polythiophene and its derivatives and copolymers, including poly(3-alkyl thiophenes) and poly(3,4-ethylenedioxythiophene) (PEDOT), polyaniline and its derivatives and copolymers, poly(p-phenylene vinylene) and its derivatives and copolymers, polysulfone and its derivatives and copolymers, and polyacetylene and its derivatives and copolymers. Polypyrrole is one of the more stable of these polymers under physiological conditions. Known derivatives of polypyrrole include the following substituted polymers: poly(N-methylpyrrole), poly(N-butylpyrrole), poly[N-(2-cyanoethyl)pyrrole], poly[N-(2-carboxyethyl)pyrrole], poly(N-phenylpyrrole), poly[N-(6-hydroxyhexyl)pyrrole], and poly[N-(6-tetrahydropyranylhexyl)pyrrole], among others.

Conductive copolymers may be formed from the above and other monomers (e.g., from pyrrole monomers, thiophene monomers, aniline monomers, p-phenylene vinylene monomers, sulfone monomers, acetylene monomers, etc). For instance, pyrrole copolymers can be formed, for example, from two or more of the following monomers: pyrrole, 1-(2-cyanoethyl)pyrrole, 1-phenylpyrrole, 3-(acetic acid)pyrrole, 1-(propionic acid)pyrrole, and the pentafluorophenol ester of the same, among others. Specific examples include, for example poly[pyrrole-co-3-(acetic acid)pyrrole], poly[pyrrole-co-1-(propionic acid)pyrrole], poly[pyrrole-co-1-(propionic acid)pyrrole pentafluorophenol ester], poly[pyrrole-co-1-(2-cyanoethyl)pyrrole] and poly(pyrrole-co-1-phenylpyrrole), among others.

Conductive polymers are typically semi-conductors in their neutral state. However, upon oxidation or reduction of the polymer to a charged state (e.g., polypyrrole is positively charged when oxidized and is neutral when reduced), the electrical conductivity is understood to be changed from a semi-conductive regime to a semi-metallic regime.

Without wishing to be bound by theory, oxidation and reduction are believed to lead to charge imbalances that, in turn, can result in a flow of ions into or out of the material. These ions typically enter/exit the material from/into an ionically conductive medium adjacent to the polymer. It generally believed that dimensional changes are effectuated in conductive polymers by the mass transfer of the ions into or out of the polymers. For example, in some conductive polymers, expansion is believed to be due to ion insertion between chains, whereas in others, inter-chain repulsion is believed to be the dominant effect. Regardless of the mechanism, this ion movement results in expansion or contraction of the polymer which can deliver significant stresses and strains. For example, E. Smela et al., "Volume Change in Polypyrrole Studied by Atomic Force Microscopy," *J. Phys. Chem. B*, 105 (2001) 9395-9405, have reported an increase in film thickness by over 35 percent for polypyrrole in the reduced state compared to the oxidized state.

Redox switching of conductive polymers may allow a number of different oxidation states to be accessible. These redox states are stabilized by charge-balancing counter ions (often called dopant ions), which move in and out of the polymer during electrochemical switching. As a specific example, a variety of charge-balancing anions may be associated with an oxidized, positively charged, conductive polymer, such as polypyrrole, for example, during electropolymerization. However, by reducing/neutralizing the polymer, a net negative charge develops within the polymer.

If the dopant anions are substantially mobile (e.g., where the anions are small molecules), the development of the net negative charge upon reduction/neutralization of the polypyrrole results primarily in expulsion of the anions from the polymer into the adjacent ionically conductive medium, shrinking the polymer. Examples of mobile ions that are commonly used in the formation of polypyrrole include perchlorate ($ClO_4^-$), $BF_4^-$, $Br^-$, $Cl^-$, $NO_3^-$, and $I^-$. Naturally occurring ions (in the body) such as chloride ions may be preferred from a biological point of view.

If the dopant anions are substantially immobile (e.g., where the anions are large molecules), the development of the net negative charge upon reduction/neutralization of the polypyrrole results primarily in an influx of cations from the adjacent ionically conductive medium, expanding the polymer. Examples of substantially immobile anions that are commonly used in the formation of polypyrrole include sulfonate salts, for example, alkyl benzene sulfonates where the alkyl group ranges from 1 to 20 carbon atoms and can be straight chain or branched, particularly, dodecyl benzene sulphonate (DBS), polyvinyl sulfonate and poly-4-styrene sulfonate, ferrocyanide, polyaspartic acid, polyglutamic acid and heparin. Examples of mobile cations include naturally occurring (in the body) cations such as $Na^+$ and $K^+$, among others.

It is noted that dodecylbenzene sulfonate is a surfactant having a hydrophilic (charged) end and hydrophobic (hydrocarbon) end. Reduction/neutralization of polypyrrole in which dodecylbenzene sulfonate is used as the dopant ion has been observed to cause an increase in hydrophilicity, which has been hypothesized to be the result of the repulsion of the charged end of the surfactant from the polymer bulk to the surface (i.e., the interface with the ionically conductive medium), such that the concentration of the hydrophilic charged end groups increases at the surface. Conversely, oxidation of the polypyrrole has been observed to cause an increase in hydrophobicity, which has been hypothesized to be the result of withdrawal of the charged end of the surfactant into the polymer bulk, leading to an increase in concentration of the hydrophobic end of the surfactant at the surface. Regardless of the mechanism, dodecylbenzene-sulfonate-doped polypyrrole is observed to swell and become more hydrophilic upon reduction/neutralization and is observed to shrink and become more hydrophobic upon oxidation. See, e.g., J. Causley et al., "Electrochemically-induced fluid movement using polypyrrole," *Synthetic Metals* 151 (2005) 60-64. The switching from hydrophobic to hydrophilic upon swelling can be used as an additional mechanism to repel enclosed particles (e.g., hydrophobic particles).

If the dopant anions are moderately mobile (e.g., where the medium-sized anions such as tosylate anions are employed), motion of both cations and anions have been observed during redox processing. K. Naoi et al., *J. Electrochem. Soc.*, Vol. 138, No. 2, February 1991, pp. 440-445.

Various conductive polymers can be formed by electropolymerization. For instance, pyrrole monomers may be electropolymerized in the presence of a suitable anionic material (e.g., one of the anionic doping materials discussed above, among others). A typical apparatus for carrying out electropolymerization includes the following: an anode (e.g., a conductive metal surface upon which electropolymerization takes place), a cathode (e.g., a metallic counter-electrode) and, frequently, a reference electrode, each separated by an electrolyte (e.g., a solution containing pyrrole and one or more suitable doping anions), as well as a potentiostat which monitors/sets the voltages/currents at the various electrodes. Electropolymerization can be carried out under a variety of electrochemical conditions including the following, among others: (a) constant current (galvanostatic), (b) constant voltage (potentiostatic), (c) current scan/sweep, e.g., via a single or multiple scans/sweeps, (d) voltage scan/sweep, e.g., via a single or multiple scans/sweeps, (e) current square waves or other current pulse wave forms, (f) voltage square waves or other voltage pulse wave forms, and (g) a combination of different current and voltage parameters.

For further regarding conductive polymers, see, e.g., Pub. Nos. US 2006/0184092 to Atanasoska et al. and US 2007/0239256 to Weber et al., as well as the references cited therein.

Therapeutic-agent containing particles for use herein can vary widely in size, for example, ranging in width from 100 micrometers ($\mu$m) or more to 50 $\mu$m to 25 $\mu$m to 10 $\mu$m to 5 $\mu$m to 2.5 $\mu$m to 1 $\mu$m to 500 nanometers (nm) to 250 nm to 100 nm 50 nm to 25 nm to 10 nm or less. For example, the width may range from 100 nm to 20 nm, a size resembling that of natural transporting systems (e.g. viruses and lipoproteins), which allow efficient cellular uptake via endocytosis. In certain embodiments, such particles are monodisperse. As used herein, "monodisperse" particles are a group of particles which are of substantially the same size, for example, having a size distribution such that at least 90 percent of the particles have widths that are within 10 percent of one another.

In various embodiments, the functionality of such particles promotes more efficient uptake once the particles are in contact with the vessel wall. For example, the nanoparticles may be coated with a cationic molecule. Various cationic polymers have been developed and successfully used for cellular uptake of nanoparticles, including, for example linear polyethyleneimine (lPEI), commercially available as jetPEI™ from Polyplus-transfection Inc., New York, N.Y., USA, polyamidoamine (PAMAM), including PAMAM dendrimers (e.g., fractured dendrimers available as Superfect® from Qiagen Inc., Valencia, Calif., USA), and poly(2-dimethylamino ethyl methacrylate) (pDMAEMA). Cationic polymers have been shown to be efficient vectors for gene delivery, and chitosan, a cationic polysaccharide, is also widely used as a gene carrier because it is a biodegradable natural polymer.

Such particles may consist essentially (i.e., contain 90 weight (wt) percent or more, preferably 95 wt percent or more, or even 99 wt percent or more) of a single therapeutic agent or a combination of two or more therapeutic agents.

In various embodiments, such particles may comprise one or more therapeutic agents encapsulated within another substance (e.g., within a capsule formed using one or more organic materials) or dispersed within a matrix that is formed from another substance (e.g., within a matrix formed using one or more matrix forming organic materials).

Specific examples of organic materials include polymers and other high molecular weight organic materials (which may be biostable or biodisintegrable, and which may have a positive charge, negative charge or neutral charge a physiological pH). Organic materials may be selected, for example, from one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes;

p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, and glycosaminoglycans such as hyaluronic acid; as well as blends and further copolymers of the above.

A wide range of therapeutic agents, several types of which are described below, may be used within the therapeutic-agent containing particles described herein.

In certain embodiments, therapeutic-agent containing particles for use herein comprise an anti-restenotic agent (e.g., paclitaxel, everolimus, serolimus, etc.). For example, chitosan is positively charged polysaccharide which has been shown to provide an excellent healing surface. In some embodiments, particles having a width ranging from 50 to 150 nm are formed in which paclitaxel is dispersed within a chitosan matrix or encapsulated in chitosan (e.g. within a single layer or via a layer-by-layer process). As another example, particles having a width ranging from 50 to 150 nm are formed in which paclitaxel is encapsulated in lecithin, a negatively charged protein.

Several nanoparticles containing anti-restenotic agents can be obtained commercially or are under development. Examples include Abraxane® an albumin-bound paclitaxel particle of approximately 130 nm in diameter that comprises albumin, a natural carrier of water-insoluble molecules. Other examples include paclitaxel and sirolimus nanoparticles, produced by Elan under the trade name NanoCrystals®, which have a selectable size of 100 nm to 1000 nm and are optimized for a high transfer into cells. Still another example is Paxceed®, poly(ethylene oxide)-b-poly(D,L-lactic acid) microparticles incorporating paclitaxel.

In certain embodiments, the medical devices of the present disclosure comprise an underlying substrate material which may be, for instance, selected from conductive and non-conductive substrate materials, examples of which include metallic materials, polymeric materials (e.g., selected from suitable members of the organic materials listed above), ceramic materials, carbon-based materials, and silicon-based materials, among many other possibilities. (As defined herein, a "conductive" material has a bulk resistivity of $10^{-4}$ ohm-cm or less (e.g., ranging from $10^{-4}$ ohm-cm to $10^{-6}$ ohm-cm to $10^{-8}$ ohm-cm or less), whereas a "nonconductive" or "insulating" material has a bulk resistivity of at least $10^3$ ohm-cm (e.g., ranging from $10^3$ ohm-cm to $10^5$ ohm-cm to $10^7$ ohm-cm to $10^{10}$ ohm-cm or more).

Various embodiments of the present disclosure will now be described in which the electroactive polymer material is disposed within the bottom of a depression (e.g., a pore, a trench, etc.) thereby forming a reservoir in the upper part of the depression. When the electroactive polymer material swells upon actuation, the volume of the reservoir is reduced (or eliminated), and the particles are pushed from the reservoir.

Figure 4A:
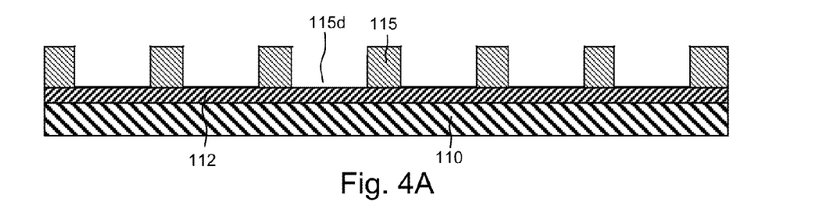
FIGS. 4A-4C are schematic cross-sectional views illustrating a method of forming a portion of a medical device in accordance with an embodiment of the present disclosure.

Construction of such devices will be described in FIGS. 4A-4C. FIG. 4A is a schematic cross-sectional view, illustrating a portion of a medical device substrate 110 in accordance with the present disclosure. The cross section of FIG. 4A may correspond, for example, to a portion of a substrate of an implantable or insertable medical device. The substrate 110 shown is a non-conductive substrate.

For example, the medical device substrate 110 shown may correspond to a portion of a medical balloon. Suitable substrate materials for medical balloons include non-compliant materials, for example, non-compliant polymeric materials such as polyamide homopolymers and copolymers, for instance, a nylon material such as nylon 12 (e.g., Vestamid®) or a polyamide-polyether block copolymer, for instance a poly(tetramethylene oxide)-polyamide-12 block copolymer, available from Elf Atochem as PEBAX. Suitable substrate materials for medical balloons further include compliant materials including compliant polymeric materials such as silicone rubber, polyurethane, latex or polyisoprene. In this regard, the medical device may correspond to a wide variety of balloon catheters, including those with compliant balloons, non-compliant balloons, fiber balloons, braided balloons and/or cutting balloons. (Note that the blades on the cutting balloons may be used as counter-electrodes in certain embodiments of the present disclosure.)

A conductive layer 112 (e.g., gold, platinum, etc.) is disposed over the non-conductive substrate 110.

As used herein a "layer" of a given material is a region of that material whose thickness is small (e.g., 25 percent or less) compared to both its length and width. As used herein a layer need not be planar, for example, taking on the contours of an underlying substrate. Layers can be discontinuous (e.g., patterned). Layers can be stacked. Terms such as "film," "layer" and "coating" may be used interchangeably herein.

For example, the conductive layer 112 in FIG. 4A may be deposited on the non-conductive substrate 110 electrochemically (e.g., by electro- or electroless-deposition), by chemical vapor deposition (CVD), or by physical vapor deposition (PVD) (e.g., sputter deposited, etc.), among other techniques.

Although not shown, an intermediate layer may be provided between the substrate 110 and conductive layer 112 in certain embodiments. For example, an intermediate layer may be provided to promote adhesion between the substrate 110 and the conductive layer 112. For instance, where the substrate is a polymeric substrate, a metal oxide layer such as a chromium oxide layer may be deposited (e.g., by CVD, PVD, etc.) on the polymeric substrate prior to deposition of the conductive layer 112.

Figure 4B:
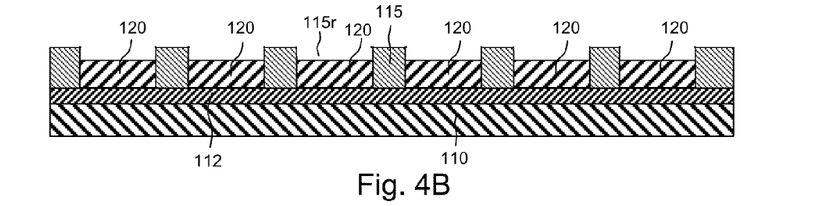
Figure 4C:
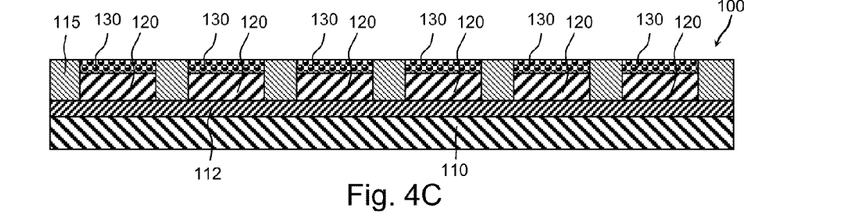

A conductive layer 112 is employed in FIGS. 4A-4C, because the substrate is non-conductive. On the other hand, in embodiments where the medical device comprises a conductive substrate, for instance, a metallic stent, metallic balloon, etc. one may dispense with the additional conductive layer entirely, if desired. Thus, statements pertaining to the conductive layer 112 in the description to follow are also applicable to conductive substrates.

The conductive layer 112 is configured for electrical communication with a source of electrical power. For example, the conductive layer 112 may be connected to a source of electrical power that is disposed within the device, or it may be connected to a source of electrical power that is remote from the device. For instance, in some embodiments, the conductive layer 112 may be connected (e.g., by means of conductive cables) to a power supply that is disposed within a console or other external device that is operable by a healthcare provider.

Disposed over the conductive layer 112 is an insulating material layer 115, which contains a plurality of apertures that extend entirely through the insulating material layer 115 to the conductive layer 112. The apertures form a series of depressions 115d (e.g., pores, trenches, etc.) associated with the insulating material layer 115. The layer of insulating material 115 may be formed, for example, from a ceramic material (e.g., a metal or semi-metal oxide) or a non-conductive polymeric material, among other materials, with the apertures formed either via selective material removal or selective material deposition.

In one embodiment, a suitable polymeric material (e.g. selected from suitable members of the polymers listed above, for instance, a polyurethane, styrene-isobutylene block copolymer, silicone, among many others) is deposited over the conductive layer (e.g., a gold layer, platinum layer, etc.) by a suitable technique (e.g., spray coating, dip coating, etc.). Consequently, a laser (e.g., an excimer laser, etc.) may be used to ablate apertures in the polymeric material and expose the conductive layer underneath. Because metals typically require much higher energy density to ablate than polymers, it is relatively easy to remove the polymer without significantly impacting the metallic material lying below the polymer. The device may be provided with indexing features to improve the accuracy of the laser ablation process.

Figures 2, 3:
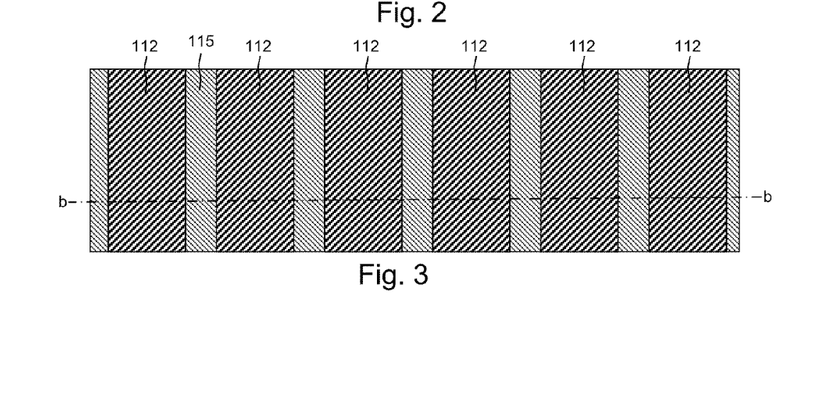
FIGS. 2 and 3 are schematic top views of a portion of a surface of a medical device in accordance with an embodiment of the present disclosure.
Figure 6:
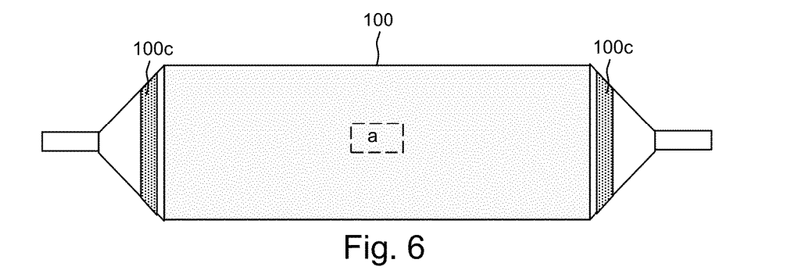
FIG. 6 is a schematic illustration of a balloon in accordance with an embodiment of the present disclosure.

As noted above, the insulating material layer 115 can be provided with apertures having a variety of shapes. For example in some embodiments the apertures can be in form of pores (e.g., round pores, oval pores, polygonal pores, etc). An example of such a device is shown in the schematic top view of FIG. 2, in which one looks into pores formed in the insulating material layer 115 which extend down to the conductive layer 112. FIG. 2 may correspond, for example, to a fraction of the surface area a of a medical balloon 100 as shown in FIG. 6 (also shown on the cones of the balloon of FIG. 6 are counter-electrodes 100c). In this embodiment, the cross-section of FIG. 4A may correspond to a section taken along line b-b in FIG. 2.

In alternative embodiments, the apertures can be in form of trenches. An example of such a device is shown in the schematic top view shown in FIG. 3, in which one looks into a series of trenches formed in the insulating material layer 115 which extend down to the conductive layer 112. As with FIG. 2, FIG. 3 may correspond, for example, to a fraction of the surface area a of a medical balloon 100 as shown in FIG. 6. In this embodiment, the cross-section of FIG. 4A may correspond to a section taken along line b-b in FIG. 3.

Turning now to FIG. 4B, in a next step, the bottoms of the depressions 115d are filled with an electroactive polymer material 120. For example, electroactive polymer material 120 may correspond to a series of electroactive polymer pillars within pores in the insulating material layer 115 (see, e.g., FIG. 2). As another example, the electroactive polymer material 120 may correspond to a series of electroactive polymer strips within trenches in the insulating material layer 115 (see, e.g., FIG. 3). Regardless of the shape, the thickness of the electroactive polymer material 120 is dictated by the thickness of the insulating material layer 115 and the percent increase in the thickness of the electroactive polymer material 120 upon electrical actuation. For example, assuming a 50 percent increase in the thickness of the electroactive polymer material 120 upon actuation, the thickness of the electroactive polymer material 120 may be 66.7 percent or more of the thickness of the insulating material layer 115 prior to activation in order that the thickness of the electroactive polymer material 120 will be 100 percent or more of the thickness of the insulating material layer 115 after activation. Typically, the thickness of the electroactive polymer material 120 will be 50 percent to 90 percent (e.g. 50 percent to 60 percent to 70 percent to 80 percent to 90 percent) of the thickness of the insulating material layer 115.

As a specific example, an electroactive polymer material 120 (e.g., polypyrrole, etc.) may be electro-polymerized on the exposed portions of the conductive layer 112 in the presence of a suitable dopant ion (e.g., dodecylbenzene sulfonate, etc.). The electro-polymerization may proceed at a relatively low charge transfer (see, e.g., the Example below) such that the growth of the electroactive polymer material 120 is limited to a few micrometers per hour. The growth is stopped when the electroactive polymer material 120 reaches a desired fraction of the thickness of the insulating material layer 115 (e.g., 60-80 percent). (As previously noted, in the embodiment shown in FIG. 4B, the substrate material is non-conductive, necessitating the application of a conductive layer prior to electropolymerization. If the substrate is conductive, on the other hand, the electroactive polymer can be electropolymerized directly on the substrate.)

Because the depressions 115d are not completely filled, a plurality of shallow reservoirs 115r remain in the insulating material layer 115. In a subsequent step, therapeutic-agent containing particles 130 are placed in the shallow reservoirs 115r as shown in FIG. 4C.

The therapeutic-agent containing particles may be loaded into the reservoirs, for example, by introducing a suspension of the particles into the reservoirs (e.g., utilizing an inkjet printer system). Such devices have an advantage that one can define the amount of therapeutic-agent containing particles that are deposited into each individual reservoir. In some embodiments, the device may be provided with indexing features to improve the accuracy of the filling processes. In other embodiments, particles may be loaded using a camera-based system to locate the holes. For example, polypyrrole is black, whereas many insulating polymers such as polyurethane can be chosen to be transparent or white, allowing for ready identification of the reservoirs. For instance, such a system may employ a camera to recognize the reservoirs and send a signal to a disposing head to dispense drops in the depressions recognized by the camera system. For examples of suitable systems for loading the devices of the present disclosure, see, e.g., U.S. Pat. No. 7,048,962 to Shekalim et al. and U.S. Pat. No. 6,676,987 to Zhong et al.

As noted above, in certain embodiments, one or more counter-electrodes may be provided on the medical device. For example, in the case of a medical balloon, one or more counter-electrodes (e.g., formed of a suitable metal such as platinum, gold or copper, or formed from a suitable electroactive polymer such as polypyrrole, among other possibilities) may be deposited on the ends (typically cone-shaped) of the balloon. Two such counter-electrodes 100c are shown in FIG. 6. In other embodiments, counter-electrodes may be provided on the device surface between the depressions. As with the conductive layer 112 (see, e.g., FIG. 4C), the counter-electrode(s) is/are configured for electrical communication with a source of electrical power, which may be, for example disposed within the device, remote from the device, and so forth. For example, the counter-electrode(s) may be connected (e.g., by means of conductive cables) to a power supply that is disposed within a console or other device that is operable by a healthcare provider, in certain embodiments.

Figure 7:
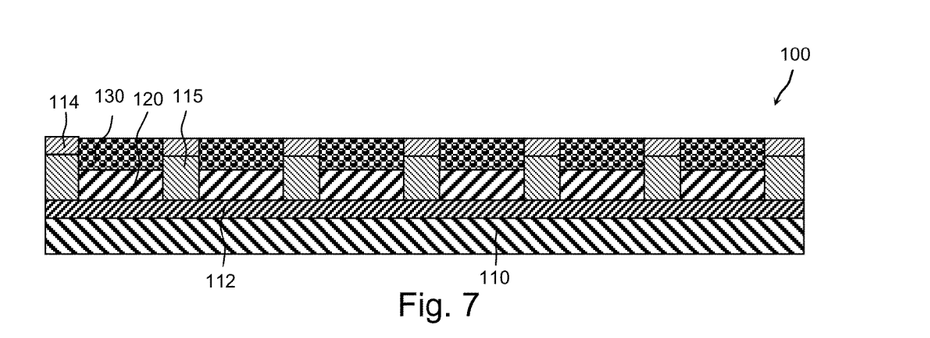
FIG. 7 is a schematic cross-sectional view illustrating a portion of a medical device in accordance with an embodiment of the present disclosure.

An example of a device in which counter-electrodes are provided on the device surface between the depressions is shown in FIG. 7. Referring now to FIG. 7 there is shown a medical device 100 that is similar to that of FIG. 4C in that the device 100 includes a substrate 110, conductive layer 112, insulating material layer 115, electroactive polymer material 120, and therapeutic-agent containing particles 130. FIG. 7, however, further includes a conductive layer 114 disposed on the top of the insulating material layer 115. The conductive layer 114 has apertures that correspond to the apertures in the insulating material layer 115. Like the conductive layer 112, the conductive layer 114 is configured for electrical communication with a source of electrical power, such that the conductive layer 114 is able to act as a counter-electrode.

In addition, one or more reference electrodes may also be provided on the medical device in order to give feedback to the power supply. For example, as with the counter-electrodes, in the case of a medical balloon, one or more reference electrodes (e.g., silver-based reference electrode, copper-based reference electrode, etc.) may be deposited on the ends of the balloon. In other embodiments, reference electrodes may be provided on the device surface between the depressions.

Upon application of a suitable potential between the electroactive polymer material (via the conductive layer) and counter-electrode in the presence of a suitable electrolyte that is disposed between the electroactive polymer material and the counter-electrode (e.g., a physiological fluid such as urine or blood, not shown), the electroactive polymer within the electroactive polymer material changes its oxidation state, resulting in a swelling of the electroactive polymer material, which pushes the particles from the reservoir.

Figure 5A:
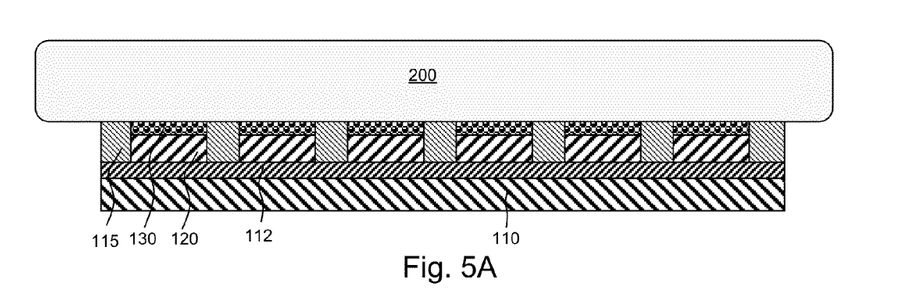
FIG. 5A is a schematic cross-sectional view of a portion of a medical device in accordance with an embodiment of the present disclosure wherein the device is in contact with bodily tissue.
Figure 5B:
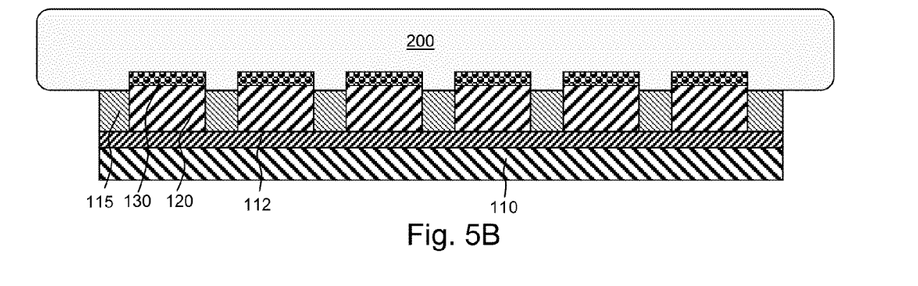
FIG. 5B illustrates the device of FIG. 1A after actuation of an electroactive polymer material within the device.

In certain embodiments, the electroactive polymer material protrudes from the reservoirs (e.g., protrudes from the apertures in the insulating material layer) upon actuation, for example, as shown in FIG. 5B (discussed below). For instance, upon actuation, the electroactive polymer material may protrude from the reservoirs by an amount ranging from 100 nm or less to 250 nm to 500 nm to 1 µm to 2 µm to 5 µm to 10 µm to 20 µm to 50 µm to 100 µm or more.

For example, the electroactive polymer material may comprise polypyrrole that is electrodeposited with large substantially immobile anions for a doping material, which is not reduced prior to loading with the therapeutic-agent-containing material. Once the device is inserted into the body of a subject, the polypyrrole is reduced/neutralized by application of a suitable potential, resulting in the influx of cations (e.g., $Li^+$, $Na^+$, $K^+$, etc.) from the surrounding physiological fluid.

As another example, the electroactive polymer material may comprises polypyrrole that is electrodeposited with small anions for a doping material, followed by reduction and expulsion of the ions prior to loading with the therapeutic-agent containing particles. Once the device is inserted into the body of a subject, the polypyrrole is oxidized, resulting in the influx of anions (e.g., $Cl^-$, etc.) from the surrounding physiological fluid and swelling of the electroactive polymer material.

An actuation process like that described above is shown in FIGS. 5A-5B. Once the device 100 is properly positioned against bodily tissue 200 as shown in FIG. 5A (e.g., for a balloon, once the balloon is inflated against a blood vessel wall) a suitable potential is applied between the electroactive polymer material 120 and one or more counter-electrodes (which may be, for example, on the cones of the balloon, among other possibilities). This causes the electroactive polymer material 120 to expand as shown in FIG. 5B, driving the therapeutic-agent containing particles 130 beyond the insulating material layer 115. As a result, the contact pressure between the therapeutic-agent containing particles and the vessel wall increases dramatically from nearly zero (when the particles 130 are in the reservoir) to a much higher value when electroactive polymer material 120 extends outside of the insulating material layer 115. The protruding "whiskers" of electroactive polymer material 120 (e.g., in the case where pores are formed in the insulating material layer 115) may also function to break through and drive the particles into the surrounding tissue.

In certain embodiments, the therapeutic-agent containing particles within the reservoir are covered with a barrier layer to prevent premature release of the particles. In various embodiments, the barrier layer that is selected is permeable to small ions in solution (e.g., $Cl^-$, $Li^+$, $Na^+$, $K^+$, etc.). Examples of barrier layers include porous layers formed from brittle materials such as mono-, di- and poly-saccharides, iodine-substituted aromatic compounds such as iopromide, polyvinyl alcohol, amylose, dextran, heparin and chitosan (many materials are brittle if deposited in sufficiently thin layers). Porous layers can be established in such materials, for instance, by a spraying process in which spray droplets of barrier material in a suitable solvent are nearly dry upon striking the surface, allowing the formation of interconnected network of partly fused particles of barrier material. As another example, thin inorganic coatings of ceramic materials (e.g., a ~20 nm layer of $TiO_2$ or $Al_2O_3$) may be created by Atomic Layer Deposition (ALD). In this regard, $Al_2O_3$ is permeable when deposited at low temp using ALD.

Further examples of barrier layers include material layers that dissolve over the time frame that is employed to implant/insert the device at the position desired for particle delivery (and thus need not be permeable to ions). Examples of such materials include mannitol, polyethylene glycol and amphiphilic molecules such as phospholipids, cholesterol, glycolipids, fatty acids, bile acids and saponins, among others.

In still further examples, pH sensitive materials may be employed as barrier layers to prevent premature release of the therapeutic-agent containing particles from the reservoirs of the device. For example, a material that is insoluble at physiological pH but soluble at slightly acidic pH or at slightly basic pH may be employed for this purpose. A nearby electrode, for example, an electrode within the reservoir or a electrode adjacent the barrier layer on the surface of the device, may be provided with a suitable bias to change the pH of the local environment, dissolving the material. For instance, a suitable anodic bias may be applied to supply electrogenerated acid or a suitable cathodic bias may be applied to supply electrogenerated base. In some instances, such materials may be crosslinked to provide pH swellable and contractable gels. Examples of such materials include materials which are insoluble at physiological pH and become soluble at slightly acidic pH, for instance, materials that have functional groups (e.g., amines, etc.) that become protonated and converted into charged groups (e.g., ammonium, etc.) at slightly acidic pH, causing the material to be soluble in water/blood. One specific example of a material that becomes soluble at slightly acidic pH is chitosan. Examples of such materials further include materials which are insoluble at physiological pH and become soluble at slightly basic pH, for instance, materials that have functional groups (e.g., —COOH, etc.) that become deprotonated and converted into charged groups (e.g., —$COO^-$, etc.) at slightly basic pH, causing the material to be soluble in water/blood. One specific example of a material that becomes soluble at slightly basic pH is starch.

Where the counter-electrode is positioned on a distinct device, one may be able to preferentially change the oxidation state of the electroactive polymer on specific regions of the medical device containing the reservoirs, preferentially releasing the particles from certain regions of the medical device but not others. For example, one may wish to advance an angioplasty balloon system, with reservoirs/depots fully covering the cylindrical portion of the balloon surface, along a first guidewire into the main branch of a bifurcation in the vasculature. A distinct counter-electrode device may be positioned on a separate guidewire which is positioned in a side branch of the bifurcation. When the counter-electrode and electroactive polymer materials on the balloon are provided with a suitable bias, the reservoirs in the vicinity of the side branch are activated faster than those opposing the side branch (due to current distribution effects).

As another example, an implant may be implanted, followed by particle release from only a specific region on the surface of the device. For instance, one may wish to preferentially release particles from a region of the medical device where tissue regeneration is going more slowly compared to other regions of the device. For example, one may place a counter-electrode (e.g., an insulated conductive needle with a non-insulated tip, etc.) in the vicinity of the slower regenerating area, releasing there a certain amount of therapeutic agent.

Examples of tissue regenerating materials include, for example, growth factor stimulating hormones and factors such as progesterone, estrogen, methyl-prednisolone, tri-amzinolone-acetate, corticosteroid, insulin, PDGF (platelet-derived growth factor), purpurin and activin, among others. Further examples of growth factors include, acid fibroblast growth factor (aFGF), basic fibroblast growth factor bFGF, bone morphogenetic protein (BMP), recombinant human bone morphogenetic protein (rhBMP), epidermal growth factor (EGF), hepatocyte growth factor (HGF), insulin-like growth factor I (IGF-I), nerve growth factor (NGF), transforming growth factor (TGF) and vascular endothelial growth factor (VEGF).

As seen from the above, various embodiments of the present disclosure involve the formation of depressions at the medical device surface, which depressions ultimately form reservoirs for the therapeutic agent. Examples of depressions include pores and trenches, which may be formed in a great variety of shapes and sizes. Examples include pores whose lateral dimensions are circular, polygonal (e.g., triangular, quadrilateral, penta-lateral, etc.), as well as pores of various other regular and irregular shapes and sizes. Multiple depressions can be provided in a near infinite variety of arrays. Trenches include simple linear trenches, wavy trenches, trenches formed from linear segments whose direction undergoes an angular change (e.g., zigzag trenches), and linear trench networks intersecting at various angles, as well as other regular and irregular trench configurations. The depressions can be of any suitable size that provides the features of the present disclosure. For example, the medical devices of the present disclosure typically contain depressions whose smallest lateral dimension (e.g., the width) is less than 10 mm (10,000 μm), for example, ranging from 10,000 μm to 1,000 μm to 100 μm to 10 μm to 1 μm to 100 nm or less. In certain embodiments the smallest lateral dimension (e.g., the width) is on the order of 1 to 2 to 5 to 10 to 20 to 50 to 100 μm. The depth of the depression may be independent of the width of the depression but is generally on the order of magnitude as the depression width. For example, the depth of the depression may range from 10,000 μm to 1,000 μm to 100 μm to 10 μm to 1 μm to 100 nm or less (e.g., 1 to 2 to 5 to 10 to 20 to 50 to 100 μm).

Examples of techniques for forming depressions include direct removal techniques as well as mask-based removal techniques, in which masking is used to protect material that is not to be removed. Direct removal techniques include those in which material is removed through contact with solid tools (e.g., microdrilling, micromachining, etc.) and those that remove material without the need for solid tools (e.g., those based on directed energetic beams such as laser, electron, and ion beams). Mask-based techniques include those in which the masking material contacts the material to be machined (e.g., where masks are formed using known lithographic techniques) and techniques in which the masking material does not contact the material to be machined, but which is provided between a directed source of excavating energy and the material to be machined (e.g., opaque masks having apertures formed therein, as well as semi-transparent masks such as gray-scale masks which provide variable beam intensity and thus variable machining rates). Material is removed in regions not protected by the above masks using any of a range of processes including physical processes (e.g., thermal sublimation and/or vaporization of the material that is removed), chemical processes (e.g., chemical breakdown and/or reaction of the material that is removed), or a combination of both. Specific examples of removal processes include wet and dry (plasma) etching techniques, and ablation techniques based on directed energetic beams such as electron, ion and laser beams.

"Therapeutic agents," drugs," "bioactive agents, "pharmaceuticals," "pharmaceutically active agents", and other related terms may be used interchangeably herein and include genetic and non-genetic therapeutic agents.

Therapeutic agents may be used singly or in combination. In the preceding embodiments, the medical devices of the present disclosure are described as delivering a single type of particle (which may contain one or more therapeutic agents). In other embodiments, multiple types of particles may be delivered.

In embodiments pertaining to the treatment of restenosis (e.g., where the device is a drug-delivering medical balloon) it may be desirable to deliver a vasodilating agent and an antirestenotic agent. Such multiple agents may be supplied, for instance, using a single type of particle. On the other hand, such multiple agents may be released within using multiple types of particles, for example, by employing a first population of particles that contain a first agent (e.g., the vasodilating agent) and a second population of particles that contain a second agent (e.g., the antirestenotic agent). The first and second populations of microparticles can be admixed and loaded into the reservoir(s) of the device, thereby resulting in the two populations of particles being delivered concurrently, although the two populations of particles may have differing release characteristics in vivo (e.g., it may be desirable to employ particles that release the vasodilating agent prior to the antirestenotic agent). Alternatively, the first and second populations of microparticles can be loaded in separate reservoirs, allowing them to be delivered at different times. For instance, it may be desirable to deliver the first population (which contains the vasodilating agent) before delivery of the second population (which contains the antirestenotic agent). In one example, alternating reservoirs (trenches) of the device may be supplied with differing microparticle populations. In another example, alternating reservoirs (pores) of the device may be supplied with differing microparticle populations (e.g., in a "checkerboard" fashion).

A wide range of therapeutic agent loadings can be used in conjunction with the devices of the present disclosure, with the pharmaceutically effective amount being readily determined by those of ordinary skill in the art and ultimately depending, for example, upon the condition to be treated, the nature of the therapeutic agent itself, the tissue to which the device is introduced, the release characteristics of the therapeutic agent, and so forth.

Therapeutic agents include non-ionic therapeutic agents, cationic therapeutic agents and anionic therapeutic agents.

Exemplary therapeutic agents for use in conjunction with the present disclosure may be selected, for example, from the following, among others: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, and (gg) VLA-4 antagonists and VCAM-1 antagonists.

Numerous therapeutic agents, not necessarily exclusive of those listed above, have been identified as candidates for vascular treatment regimens, for example, as agents targeting restenosis (antirestenotics). Such agents are useful for the practice of the present disclosure and may be selected, for example, from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), olimus family drugs such as sirolimus, everolimus, tacrolimus and zotarolimus, Epo D, dexamethasone, purine antagonists/analogs such as 6-mercaptopurine, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives and prodrugs of the forgoing, among others.

Numerous additional therapeutic agents useful for the practice of the present disclosure are also disclosed in U.S. Pat. No. 5,733,925 to Kunz, the entire disclosure of which is incorporated by reference.

EXAMPLE

A chromium oxide layer approximately 20 nm in thickness is sputter deposited as an adhesion layer on the cylindrical portion of the surface of a poly(tetramethylene oxide)-polyamide-12 block copolymer angioplasty balloon shaped like that of FIG. 6. The chromium oxide film is deposited using a RF-magnetron sputtering system, MRC 8667 (Material Research Corp.), using a 99.9 percent purity chromium oxide ($Cr_2O_3$) target. A gold film approximately 50 nm in thickness is sputter deposited on the chromium oxide film. On top of this film is sprayed a polyurethane film (e.g., Pellethane® 2103-80AEN, available from Dow Chemical) of approximately 20 micrometer in thickness, which completely covers the gold film on the balloon. An excimer laser, 248 nm krypton fluoride (KrF), 16 nanosecond pulse, 20 Hertz repetition frequency, focused via a mask to deliver 500 milliJoules/cm², 110 pulses, is then is used to ablate pockets out of the polyurethane film (e.g., circular pores of approximately 10 micrometer in width), exposing the gold film underneath. Polypyrrole is electro-polymerized in the presence of dodecyl benzene sulphonate (DBS) as a doping ion, for instance, at a relatively low charge transfer (e.g., a constant charge density of 30 milliCoulombs/cm²) at 0.65 V vs. Ag/AgCl, 3 M chloride ion from 1.0 M aqueous pyrrole solution containing 1 percent dodecylbenzynesulphonate with the pH adjusted to 3.0 and the temperature maintained at 20° C., and growth is stopped when the polypyrrole pillar reaches approximately 80 percent of the polyurethane coating thickness (8 micrometer). The resulting reservoirs are loaded via an ink jet printer with a suspension of lecithin coated paclitaxel particles of approximately 100 nm in diameter in purified water. Counter-electrodes formed of platinum rings which are of approximately 50 micrometer in thickness are formed on the cones of the balloon. The gold film and the counter-electrodes are electrically connected to insulated conductors that extend along the length of a catheter shaft upon which the balloon is mounted, terminating in plugs that are suitable for connection to a power supply.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. An implantable or insertable medical device comprising: a surface with at least one depression; an electroactive polymer material positioned in the depression and adapted for electrical communication with a source of electrical power; and particles comprising a therapeutic agent disposed within the depression over the electroactive polymer material; wherein upon electrical actuation of the electroactive polymer material, the electroactive polymer material swells and the particles are delivered from the device.

2. The implantable or insertable medical device of claim 1, wherein the electroactive polymer material comprises a conductive polymer that is actuated by applying a potential that is sufficient to change the oxidation state of the conductive polymer.

3. The implantable or insertable medical device of claim 2, wherein the conductive polymer is in an oxidized state before actuation and in a reduced state after actuation.

4. The implantable or insertable medical device of claim 3, wherein the electroactive polymer material is positioned in the bottom of the depression but does not fill the depression such that a reservoir is formed in the upper portion of the depression, and wherein when the electroactive polymer material swells upon actuation, the particles are pushed from the reservoir.

5. The implantable or insertable medical device of claim 4, comprising a layer of insulating material that is disposed over a conductive material, wherein said depression corresponds to at least one aperture that is formed in the layer of insulating material and extends through the layer of insulating material to the conductive material.

6. The implantable or insertable medical device of claim 5, comprising a plurality of said apertures.

7. The implantable or insertable medical device of claim 5, wherein after actuation of the electroactive polymer material, the electroactive polymer material protrudes from the aperture.

8. The implantable or insertable medical device of claim 7, wherein the conductive polymer material fills the aperture to a height that is at least 50 percent of the thickness of the nonconductive material.

9. The implantable or insertable medical device of claim 5, further comprising a nonconductive material beneath the conductive material.

10. The implantable or insertable medical device of claim 1, wherein the medical device comprises a counter-electrode.

11. The implantable or insertable medical device of claim 1, wherein the medical device comprises the source of electrical power.

12. The implantable or insertable medical device of claim 1, wherein the medical device is adapted for electrical connection with an external power supply.

13. The implantable or insertable medical device of claim 1, wherein the device is an elongated device that comprises an insulated electrical conductor that is in electrical contact with the electroactive polymer material.

14. The implantable or insertable medical device of claim 1, wherein the depression is in the form of a trench or a pore.

15. The implantable or insertable medical device of claim 1, wherein the depression is in the form of a circular, oval or polygonal pore.

16. The implantable or insertable medical device of claim 1, wherein the medical device is an insertable device comprising an elongate shaft and a radially expandable member.

17. The implantable or insertable medical device of claim 1, wherein the radially expandable member is a balloon.

18. The implantable or insertable medical device of claim 1, wherein the particles comprise an anti-restenotic agent.

19. An implantable or insertable medical device comprising: a nonconductive substrate; a conductive layer disposed over the substrate and adapted for electrical communication with a source of electrical power; an insulating material layer disposed over the conductive layer that comprises at least one aperture that extends through the insulating material to the conductive layer; an electroactive polymer material positioned in the aperture in electrical contact with the conductive material, but not filling the aperture such that a reservoir is formed in an upper portion of the aperture; particles comprising a therapeutic agent disposed within the reservoir; and a counter-electrode adapted for electrical communication with said source of electrical power; wherein upon actuation of the electroactive polymer material by application of an electrical potential between the electroactive polymer material and the counter-electrode, the electroactive polymer material expands and pushes the particles from the reservoir.

20. The implantable or insertable medical device of claim 19, wherein the non-conductive substrate is a medical balloon.

* * * * *